US00PP10775P

United States Patent [19]

Wain

[11] Patent Number: Plant 10,775

[45] Date of Patent: Feb. 2, 1999

[54] CHRYSANTHEMUM PLANT NAMED 'CANDY TIME'

[75] Inventor: Peter Wain, Hayling Island, United Kingdom

[73] Assignee: Cleangro, Ltd., West Sussex, England

[21] Appl. No.: 838,355

[22] Filed: Apr. 8, 1997

[51] Int. Cl.[6] ..... A01H 5/00

[52] U.S. Cl. ..... Plt./76

[58] Field of Search ..... Plt./76, 81

*Primary Examiner*—Howard J. Locker

*Attorney, Agent, or Firm*—Christie, Parker & Hale, LLP

[57] ABSTRACT

A new and distinct cultivar of Chrysanthemum plant producing pink/lavender flowers with nearly white outer ray florets and a darker center.

1 Drawing Sheet

BACKGROUND OF THE INVENTION

The present invention is directed to a new and distinct variety of chrysanthemum botanically classified as *Dendranthema grandiflora*. The varietal denomination of the new Chrysanthemum is 'Candy Time.'

The female and male parents of the new variety are undistributed, unpatented seedlings identified as P52-1 and P10-2, respectively. The new variety has been asexually reproduced by vegetative cuttings in Ventura County, Calif. and the distinguishing characteristics are retained through successive generations of asexual reproduction.

SUMMARY OF THE INVENTION

'Candy Time' is a pot forcing chrysanthemum plant variety that may be grown as a disbud or spray type plant producing pink/lavender flowers with nearly white outer ray florets and a dark center, and capable of being grown commercially in a greenhouse.

BRIEF DESCRIPTION OF ILLUSTRATION

The accompanying photograph shows a typical specimen of the new variety with colors being as nearly true as possible with illustrations of this type. The illustration shows 'Candy Time' grown as a pinched spray pot mum.

DESCRIPTION OF THE PLANT

The following description of the new variety is of specimens grown in a greenhouse in Oxnard, Ventura County, Calif. in the month of October. 'Candy Time' has not been observed under all possible environmental conditions. The phenotype may vary significantly with variations in the environment such as temperature, light intensity, day length and cultural conditions. Color values are taken from The Royal Horticultural Society Colour Chart.

Plants of the new variety have been grown successfully under temperature conditions averaging about 65° F. at night and about 75°–85° F. during the day under light conditions of about 5,000–6,000 foot candles. The plants respond well to use of growth retardant, such as B-9 treatment at about 2000 ppm. To produce a commercial product the plants may be pinched twice and disbudded. It has been observed that the shelf life of 'Candy Time' is about 18 days with the response time of about 9 weeks.

Plant

Habit: Upright.
Height: About 34cm after treatment with growth regulator as described.
Branching characteristics: Fair branching.
Number of breaks from pinch: About 2–3.
Typical container size to be grown in: 4", 5", 6", 8", 10".
Length of lateral branches:
*Average.*—About 28cm.
Stem color: Near 147D.

Foliage

Leaf arrangement: Alternate.
Number of leaves per lateral branch:
*Average number of leaves per lateral branch.*—About 16 fully mature leaves per lateral branch, average leafiness.
(1) *Size.*—Length — Average about 8.5cm. Width — Average about 5.8cm.
(2) *Shape.*—Ovate.
(3) *Attachment.*—Petioled.
(4) *Apex.*—Acute.
(5) *Base.*—Tapered.

| (6) Color: | Mature | Young |
|---|---|---|
| Top: | Near 147A | Near 137A |
| Bottom: | Near 147B | Near 138A |

Margin: Deeply lobed, slightly dentate.
Aspect: Mostly flat, slightly cupped under.
Surface Characteristics:
*Top.*—Tomentose-lightly.
*Bottom.*—Puberulent.
Venation: Palmately net; main veins prominent on underside of leaf; main vein coloration near 138A, veinlet coloration near 137C.
Petiole:
(1) *Length.*—Average about 1.6cm .
(2) *Color.*—Near 147D.
Stipule: 2 at most mature nodes, 1 or 2 lobed, average about 1cm long and 0.8cm wide.

Flower

Inflorescence form: Cyme.
Flower form: Decorative.
Flower shape: Circular.

Flower color (general): Pink/lavender with nearly white outer ray florets and dark center.

Blooms: Disbudded, 1 per branch; 5 to 6 blooms per branch when produced as a spray.

(1) *Diameter.*—Average about 8.5cm.

(2) *Depth.*—Average about 3.5cm.

(3) *Longevity on plant.*—About 18 day shelf life.

*Fragrance.*—Medium, musky.

Sepal:

(1) *Number.*—About 36.

(2) *Color.*—Near 137A.

(3) *General appearance.*—Very membraneous edges, brown tips.

Peduncle:

(1) *Length.*—Terminal peduncle length about 4 cm; longest lateral peduncle length about 7 cm.

(2) *Surface.*—Lightly pubescent.

(3) *Strength.*—Very sturdy.

Bud:

(1) *Shape.*—Flattened sphere.

(2) *Diameter.*—Avg. about 1.1cm.

(3) *Color.*—Near 138B.

(4) *Height.*—About 0.6cm.

Ray florets:

(1) *Number per flower. Average about* 350.

(2) *Fused.*—No.

(3) *Texture.*—Some sheen.

(4) *Shape.*—Oblanceolate, wraps around itself to meet at base.

(5) *Apex.*—2 lobes, less apparent in older florets.

(6) *Base.*—Tapered.

(7) *Margin.*—Entire.

(8) *Aspect.*—Flat.

(9) *Length.*—Avg. About 3.5cm.

(10) *Width.*—Avg. About 1.5cm.

*Color—top side.*—Immature: Near 75C. Mature: Near 69C. Fading: Near 69D.

*Color—under side.*—Immature: Near 75C. Mature: Near 69D. Fading: Near 69D.

Disc florets: Not present.

Description of flower as it ages: Flower becomes very deep, almost spherical; fades to almost white over entire flower.

Reproductive Organs

Ray florets:

*Pistillate.*—(1) Pistil number: 1 per floret. (2) Ovary shape: Very flat sphere. (3) Stigma shape: Forked with slight outcurve. (4) Stigma color: Near 9A. (5) Style length: About 0.6cm. (6) Style color: Near 154C.

What is claimed is:

1. A new and distinct variety of Chrysanthemum plant substantially as herein shown and described.

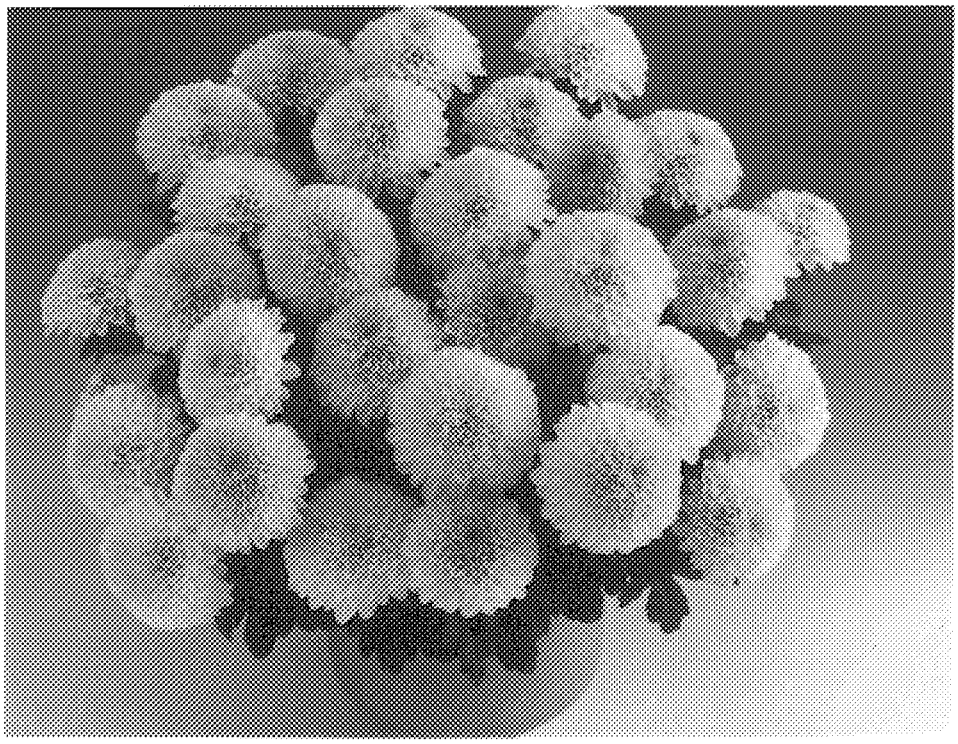

* * * * *